United States Patent [19]

Ohtsuka et al.

[11] 4,041,170
[45] Aug. 9, 1977

[54] FIELD AND GARDEN AGRICULTURAL FUNGICIDE

[75] Inventors: Takaaki Ohtsuka; Keigo Satake; Shiro Yamazaki; Nobuo Hatakeyama; Takeo Watanabe, all of Iwaki, Japan

[73] Assignee: Kureha Kagaku Kogyo Kabushiki Kaisha, Tokyo, Japan

[21] Appl. No.: 652,011

[22] Filed: Jan. 26, 1976

[30] Foreign Application Priority Data

Jan. 24, 1975 Japan .................................. 50-9686

[51] Int. Cl.$^2$ ........................................... C07D 339/08
[52] U.S. Cl. ................................. 424/277; 260/327 P
[58] Field of Search ..................... 260/327 P; 424/277

[56] References Cited

U.S. PATENT DOCUMENTS 3,249,499  5/1966  Schmeling et al. .................... 167/33

Primary Examiner—Cecilia M. S. Jaisle
Attorney, Agent, or Firm—Sughrue, Rothwell, Mion, Zinn & Macpeak

[57] ABSTRACT

2-Carbamoyl-3-N-(3',5'-dichlorophenyl)-carbamoyl-5,6-dihydro-p-dithiin-1-oxide as effective substance for the control of agricultural plant diseases.

4 Claims, No Drawings

FIELD AND GARDEN AGRICULTURAL FUNGICIDE

This invention relates to a novel compound adapted for use as effective substance of agricultural plant disease preventing and curing agent.

The novel compound may be expressed as 2-carbamoyl-3-N-(3',5'-dichlorophenyl)-carbamoyl-5,6-dihydro-p-dithiin-1-oxide having the following general formula:

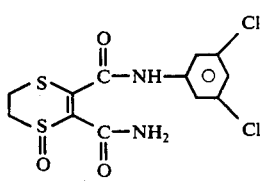
(I)

The above novel compound is highly effective for the control of a vast variety of plant diseases, among others: rice blast, downy mildew, late blight, gray mold and stem rot and the like of vegetable and fruit plants.

It has been demonstrated that the above compound represents especially superior effects in the control of various plant diseases which have become predominant with increased broader utilization of field and garden agricultural medicines. It has also been demonstrated that it has almost no phytotoxity not only to economic plants, but also to personal bodies and useful animals including fishes. It has been further demonstrated that the compound does represent substantially no residual effect in and upon plants and animals, as well as the favorable ability of easy and rapid decomposition in the earth, without inviting no practical environment fouling, thereby assuring utmost safety use and application of the compound.

The compound to this invention can be prepared in an easy way by the reaction of N-3',5'-dichloro-phenyl-5,6-dihydro-p-dithiino -2,3-dicarboxyimido-1-oxide, to be mentioned as the compound (II) throughout this specification and appended claims, with aqueous ammonia.

The starting compound (II) may be easily prepared by the reaction of, 5,6-dihydro-p-dithiino-2,3-dicarboxylic acid anhydride and 3,5-dichloroaniline to yield N-3',5'-dichlorophenyl-5,6-dihydro p-dithiino-2,3-dicarboxyimide which is then subjected to oxidation.

EXAMPLE 1

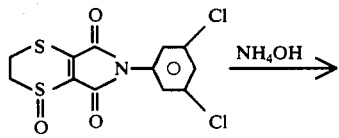
(II)

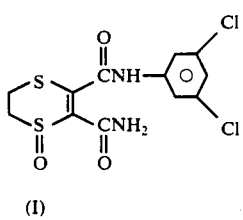
(I)

34.8 g of the material compound (II) and 250 ml of ethyl alcohol were introduced into a flask of 500 ml capacity and added with 25 g of aqueous ammonia (27%-concentration) and the mixture was agitated at room temperature for 30 minutes. The precipitated reaction product was filtered off, washed twice with acetone and dried. The product compound (I), 26.3 g, was obtained in a white powder, m.p. :160°C (with decomposition). Yield :72.0%.

The product compound (II) may be used per se, or in the form of a composition with conventional carrier or diluent. The composition may take advantageously the form of dust, emulsifiable concentrate or sprayable liquid. The composition may further be added with conventional spreader, emulsifier, wetting agent, adhesive and/or the like adjuvant(s), for improving the desired effect.

It may be further stressed that by mixing of the novel compound according to this invention with a hitherto known agricultural medicament, there is no fear of decomposition or deterioration of the compound or the partner medicament, and thus, a mixture thereof with any known fungicide, insecticide and/or fertilizer may be utilized without any fear. Successive use of these substances may be allowed without any practical difficulty.

In the following, several practical examples of compositions including the novel compound of the present invention and ready for practical use will be raised. It should be noted, however, that the kind of carrier, diluent and adjuvant and the mixing ratio of these auxiliary substance and the dosage of the effective compound may be varied in a vast range. Percentages are given by weight.

EXAMPLE 2

Dust composition

Compound (I) — 3 parts;
Clay — 40 parts;
Talc — 57 parts;

These are mixed thoroughly and evenly and pulverized into a fine dust ready for practical use by air spraying.

EXAMPLE 3

Wettable powder

Compound (I) — 30 parts;
Polyoxyethylene alkylaryl ether — 6 parts;
Kieselguhr — 64 parts;

These are mixed thoroughly and evenly and pulverized finely to provide a wettable fine powder ready for use upon dilution with proper quantity of water.

In the following, several preferred examples of the superior fungicidal effect of the novel compound according to this invention by way of biological experiments.

EXAMPLE 4

Pot test for demonstration of anti-rice blast effect

Twenty groups of pots, each being of 10 cm diameter, were provided. Each group contained three pots. Japanese rice plants, *Oryza sativa* L, variety: SASANISHIKI, of four leaf stage, were cultured in these pots. Each pot was planted with twenty stems of the rice plant. To these plants was well applied the wettable powder set forth in Example 3, after dilution with an ample amount of water to the desired concentration, to provide an aqueous suspension. The suspension was applied onto the plants by means of a liquid spray to such degree that all the leaves were well wetted. Upon drying, the leaves were inoculated with spores of rice blast fungi, *Piricularia oryzae,* by spray of an aqueous suspension thereof. Then the treated pots were placed in high humidity atmosphere at 27°–28° C for 4 days.

The uppermost leaves of rice plant stems per three pots were carefully reviewed and the observed number of lesions were counted. Equal number of pots having been untreated with the fungicidal suspension were equally inoculated as the control, and the number of lesions was counted, and the control rate was found by the following formula.

$$\text{Control rate, \%} = (1 - \frac{\text{number of lesions on treated leaves}}{\text{number of lesions on untreated leaves}}) \times 100$$

The thus determined results are shown in the following Table 1.

Table 1

| Used Agricultural medicine | Concentration, ppm | Total Number of observed lesions | Disease control rate, % | Toxicity |
|---|---|---|---|---|
| Untreated | — | 876 | — | — |
| Compound (I) | 500 | 19 | 97.8 | none |
| " | 2,000 | 0 | 100 | " |
| "Kitazin-P"* | 480 | 37 | 95.8 | " |

Remarks:
"Kitazin-P": 48%-emulsion of O,O-diisopropyl-S-benzyl thiophosphate, manufactured and sold by a Japanese firm: Kumai Kagaku Kogyo Kabushiki Kaisha, Tokyo.

EXAMPLE 5

Pot test for control of downy mildew on cucumber plants

A number of pots of 10 cm diameter, were used for the culture of cumcumber plants of two leaf stage, variety: SAGAMI hampaku. Each plant was planted in a pot. Each three pots were grouped into one treating group. To these plants was applied an aqueous suspension of the wettable powder, Example 3, which had been diluted with water. The application was made by means of a liquid spray. Upon drying, all the leaves were inoculated with spores of downy mildew fungi, *Pseudoperonospora cubensis,* by spraying. Then the plants were kept in high humidity atmosphere at 22°–23° C for 24 hours, and in a green house fo 5 days. After lapse of 5 days upon said inoculation, the degree of infection was determined by consultation with the following classification, as per one leaf per pot and per three pots for each treating district.

| | Classification |
|---|---|
| Index of infection | State of infection |
| "0" | no infection |
| "0.5" | less than 10% infection in terms of inoculated leaf area. |
| "1" | 10 – 20% infection in terms of inoculated leaf area. |
| "2" | 20 – 40% infection in terms of inoculated leaf area. |
| "3" | 40 – 60% infection in terms of inoculated leaf area. |
| "4" | 60 – 80% infection in terms of inoculated leaf area. |
| "5" | over 80% infection in terms of inoculated leaf area. |

The test results are shown in the following Table 2.

Table 2

| Used agr. medicine | Concentration, ppm | Mean index of infection | Phytotoxicity |
|---|---|---|---|
| Untreated | — | 5 | — |
| Compound (I) | 300 | 0 | none |
| Compound (I) | 2,000 | 0 | none |
| "Daconyl"* | 750 | 0 | none |

Remarks:
"Daconyl" is 75%-aqueous suspension of tetachloroisophthalonitrile, manufactured and sold by Takeda Pharmaceutical Company Limited, Osaka.

EXAMPLE 6

Pot test for the control of late blight on tomato plants

A number of pots, each being of 10 cm diameter as before, were planted each with a tomato plant at its four leaf stage, variety being FUKUJU No. 2. Each three pots were grouped into one treating district. The cultured plants were sprayed with an aqueous suspension of the wettable powder as set forth in the foregoing Example 5. An aqueous suspension of spores of tomato late blight fungi, *Phytophthora infestans,* preparatorily cultured on potato tubers were sprayed over the above treated tomato leaves upon dried. The thus conditioned plants were kept in a green house at 20°–22° C for 2 days. After lapse of four days after the said inoculation, the index of infection was determined in accordance with the foregoing classification, so as to fix the respective mean index of infection per plant. The test results are shown in the following Table 3.

Table 3

| Used. agr. medicine | Concentration, ppm | Mean index of infection | Phytotoxicity |
|---|---|---|---|
| Untreated | — | 5 | — |
| Compound (I) | 300 | 0.5 | none |
| Compound (I) | 2,000 | 0 | none |
| "Daconyl" | 750 | 0 | none |

EXAMPLE 7

Pot test for the control of gray mold on cucumber plants

A number of pots, each being of 10 cm diameter as before were planted with cucumber plants, variety being SAGAMI HAMPAKU, at its two leaf stage and in one-to-one correspondence. Each two pots were grouped into one treating district. These plants were sprayed with an aqueous suspension of the wettable powder as set forth in the foregoing Example 3. After drying, cucumber gray mold fungi, *Botrytis cinerea* Fries, preparatorily cultured on a sugar-added potato-extract-agar culture medium at 20° C for 5 days, were fixedly attached to each leaf in the ratio of two circular discs of the fungi-containing agar medium, being of 5 mm diameter, for the execution of inoculation. After inoculation, the treated plants were placed in a green house at 22°–23° C for 4 days. Two infected leaves were reviewed precisely for the determination of the mean diameter of lesions in mm. The results are shown in the following Table 4.

Table 4

| Used. agr. medicine | Concentration, ppm | Mean diameter of lesions in mm | Phytotoxicity |
|---|---|---|---|
| Untreated | — | 35.5 | — |
| Compound (I) | 300 | 0 | none |
| Compound (I) | 2,000 | 0 | none |
| "Topzin-M"* | 700 | 8.2 | none |

Remarks:
*"Topzin-M" is a 70%-aqueous suspension of 1,2-bis(3 - methoxycarbonyl-2-thioureid)benzene, manufactured and sold by a Japanese firm, Nippon Soda Company, Limited, Tokyo.

EXAMPLE 8

Pot test for the control of stem rot on kidney beans plants

A number of pots, each being of 10 cm diameter as before, were planted with kidney beans, variety: KINTOKI, at its three leaf stage. Then, the leaves of these plants were sprayed with an aqueous suspension of the wettable powder as set forth in the foregoing Example 3. After drying, we prepared two circular cuts of fungi-containing, sugar-added potato-extract-agar culture medium on which stem rot fungi, *Sclerotinia sclerotiorum* (Libert), had been preparatorily cultured. Each of these circular cuts had a 5 mm-diameter. The medicament suspension-sprayed potato plant leaves were then inoculated each with two cultured agar cuts by applying fixedly thereto and kept at 22°-23° C for 3 days in a green house. Then, two affected leaves were precisely reviewed for the determination of the mean diameter of lesions. The results are shown in the following Table 5.

Table 5

| Used. agr. medicine | Concentration, ppm | Mean diameter of lesions in mm | Phytotoxicity |
|---|---|---|---|
| Untreated | — | 39.0 | — |
| Compound (I) | 300 | 0 | none |
| Compound (I) | 2,000 | 0 | none |
| "Topzin-M" | 700 | 11.2 | none |

EXAMPLE 9

Green house test for the control of gray mold on grape plants

Test was made on house-planted grape plants in several areas of 20 m². Plants were of a variety called Canbel Early, 8 - year old. The plant leaves were sprayed with an aqueous suspension of the wettable powder as set forth in the foregoing Example 3. Spraying was carried out three times and in the ratio of 250 lit. per 10 are. More specifically, the spraying was performed May 4th, May 12th and June 1st, respectively. On July 3rd, 200 grape bunches were taken out at random among test areas and reviewed precisely them for determination of the index of infection affected by gray mold fungi, *Botrytis cinerea*. The results are shown in the following Table 6.

Table 6

| Used agr. medicine | Concentration, ppm | Index of infection, %, (on fruit bunches) |
|---|---|---|
| Untreated | — | 35.6 |
| Compound (I) | 1,000 | 5.8 |
| Compound (I) | 2,000 | 3.6 |

EXAMPLE 10

Pot test for the control of downy mildew on grape plants

Young grape plants, variety: NEO - MUSCUT, 2-year old, were planted in pots and sprayed with an aqueous suspension of the wettable powder as set forth in the foregoing Example 3, to such degree that both leaf surfaces were sufficiently wetted.

Upon drying, a second suspension of spores of downy mildew fungi, *Plasmopara viticola*, was sprayed for inoculation. These treated plants were placed in a chamber at 18°-23° C. After lapse of 10 days from the inoculation, five leaves were precisely reviewed and classified in the following way.

| Index of infection | Classification State of infection |
|---|---|
| "0" | non-infected |
| "1" | less than 25% infection in terms of total leaf area |
| "2" | 25-50% infection in terms of total leaf area |
| "3" | 50-75% infection in terms of total leaf area |
| "4" | over 75% infection in terms of total leaf area |

The results are shown in the following Table 7.

Table 7

| Used agr. medicine | Concentration, ppm | Mean index of infection | Phytotoxicity |
|---|---|---|---|
| Untreated | — | 4 | none |
| Compound (I) | 1,000 | 1 | none |
| Compound (I) | 2,000 | 0 | none |

Remarks:
Control agent was not used in these Examples 9 and 10, since no effective commercialized medicament was found out.

The embodiments of the invention in which an exclusive property or privilege is claimed are as follows:

1. 2-carbamoyl-3-N-(3',5'-dichlorophenyl)-carbamoyl-5,6-dihydro-p-dithiin-1-oxide having a general formula:

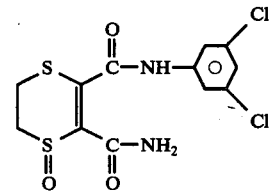

2. A fungicidal composition comprising a therapeutically effective amount of 2-carbamoyl-3-N-(3',5'-dichlorophenyl)-carbamoyl-5,6-dihydro-p-dithiin-1-oxide and a pharmaceutically acceptable carrier or diluent.

3. A dust composition as in claim 2 in which the pharmaceutically acceptable carrier or diluent is comprised of a mixture of clay and talc.

4. A wettable powder as in claim 2 in which the pharmaceutically acceptable carrier or diluent is comprised of a mixture of polyoxyethylene alkylaryl ether and Kieselguhr.

* * * * *